United States Patent
Khan et al.

(10) Patent No.: US 11,898,444 B2
(45) Date of Patent: Feb. 13, 2024

(54) CONTAMINATION ESTIMATION OF FORMATION SAMPLES

(71) Applicant: Halliburton Energy Services, Inc., Houston, TX (US)

(72) Inventors: Waqar Ahmad Khan, Houston, TX (US); Mehdi Azari, Houston, TX (US); Abbas Sami Eyuboglu, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 17/343,220

(22) Filed: Jun. 9, 2021

(65) Prior Publication Data
US 2021/0293142 A1    Sep. 23, 2021

Related U.S. Application Data

(63) Continuation of application No. 15/565,592, filed as application No. PCT/US2016/067012 on Dec. 15, 2016, now abandoned.

(51) Int. Cl.
*E21B 49/08*       (2006.01)
*G01N 9/32*        (2006.01)
(Continued)

(52) U.S. Cl.
CPC .......... *E21B 49/081* (2013.01); *E21B 49/005* (2013.01); *E21B 49/08* (2013.01);
(Continued)

(58) Field of Classification Search
CPC ...... E21B 49/08; E21B 49/082; E21B 49/086; E21B 49/0875; E21B 49/005; G01N 9/32; G01N 9/36; G01N 33/2823
See application file for complete search history.

(56) References Cited

U.S. PATENT DOCUMENTS 3,802,259 A * 4/1974 Eckels ............... G01N 33/2823
                                                    73/152.04
4,739,654 A   4/1988 Pilkington et al.
(Continued)

FOREIGN PATENT DOCUMENTS

WO    2002/052256 A1    7/2002
WO    2012/103069 A2    8/2012

OTHER PUBLICATIONS

Fadnes, Finn Hallstein, et al. "Optimization of Wireline Sample Quality by Real-Time Analysis of Oil-Based Mud Contamination—Examples from North Sea Operations." SPE Annual Technical Conference and Exhibition. Society of Petroleum Engineers, 2001.

*Primary Examiner* — Christopher J Sebesta
(74) *Attorney, Agent, or Firm* — John Wustenberg; C. Tumey Law Group PLLC (57) ABSTRACT

Contamination estimation of a mud filtrate or reservoir sample requires a robust handle on the properties of mud filtrate at downhole conditions. Coupling acquired data with downhole measured data provides a robust estimation of contamination by encompassing the entire available data. Downhole density of the mud filtrate sample may be estimated based on a characteristic of the mud filtrate sample. A density of a formation fluid of the reservoir may be determined using a formation tester tool. The contamination of the formation fluid may be estimated based on the clean fluid density and the estimated mud filtrate density by, for example, using a material balance equation or ratio. An estimated pump-out time for the formation fluid may be determined based on the estimated contamination and a trend of the estimated contamination of the formation fluid.

17 Claims, 7 Drawing Sheets

(51) Int. Cl.
*G01N 33/28* (2006.01)
*G01N 9/36* (2006.01)
*E21B 49/00* (2006.01)

(52) U.S. Cl.
CPC ............ *E21B 49/086* (2013.01); *G01N 9/32* (2013.01); *G01N 9/36* (2013.01); *G01N 33/2823* (2013.01); *E21B 49/0875* (2020.05)

(56) References Cited

U.S. PATENT DOCUMENTS

| | | | |
|---|---|---|---|
| 6,178,815 | B1 | 1/2001 | Felling et al. |
| 6,274,865 | B1 | 8/2001 | Schroer et al. |
| 6,350,986 | B1 | 2/2002 | Mullins et al. |
| 8,113,043 | B2 | 2/2012 | Crocker |
| 8,210,260 | B2 | 7/2012 | Milkovisch et al. |
| 9,023,280 | B2 | 5/2015 | Abad et al. |
| 2005/0182566 | A1 | 8/2005 | DiFoggio |
| 2006/0241866 | A1 | 10/2006 | DiFoggio |
| 2007/0119244 | A1 | 5/2007 | Goodwin et al. |
| 2008/0105032 | A1 | 5/2008 | Reddy et al. |
| 2008/0141767 | A1 | 6/2008 | Raghuraman et al. |
| 2013/0311099 | A1 | 11/2013 | Eyuboglu et al. |
| 2014/0180591 | A1* | 6/2014 | Hsu ........................ E21B 49/10 702/8 |
| 2014/0224474 | A1* | 8/2014 | Cernosek ............... E21B 49/081 166/107 |
| 2014/0260586 | A1* | 9/2014 | Van Hal ................. E21B 49/082 73/152.11 |
| 2015/0068736 | A1* | 3/2015 | Dirksen ................. E21B 33/12 166/162 |
| 2016/0090836 | A1* | 3/2016 | Wang ..................... E21B 49/08 702/12 |
| 2016/0186559 | A1 | 6/2016 | Wang et al. |
| 2016/0319662 | A1* | 11/2016 | Zuo ..................... G01N 33/2823 |

* cited by examiner

CONTAMINATION ESTIMATION OF FORMATION SAMPLES

CROSS-REFERENCE TO RELATED APPLICATIONS

The present application is continuation of U.S. patent application Ser. No. 15/565,592 filed on Oct. 10, 2017, which is a U.S. National Stage Application of International Application No. PCT/US2016/067012 filed Dec. 15, 2016, which are incorporated herein by reference in their entirety for all purposes.

TECHNICAL FIELDS

The present disclosure relates generally to testing and evaluation of subterranean or subsea formation fluids or samples, and more specifically (although not necessarily exclusively), to systems and methods for improving the contamination estimation of samples using a formation tester.

BACKGROUND

To evaluate prospects of an underground hydrocarbon reservoir, a representative sample of the reservoir fluid may be captured for detailed analysis. A sample of the reservoir fluid may be obtained by lowering a tool having a sampling chamber into the wellbore at a predetermined or sampling depth and fluid is allowed to flow into the sampling chamber. After the sample is collected, the tool may be withdrawn from the wellbore so that the sample of reservoir fluid may be analyzed.

Fluid analysis is possible using pump-out formation testers that provide downhole measurements of certain fluid properties and enable collection of a large number of representative samples stored at downhole conditions. Generally, a wellbore is filled with a drilling fluid, for example, a mud. The drilling fluid may be water-based or oil-based, is used as a lubricant and aids in the removal of cuttings from the wellbore. The drilling fluid also is used to maintain a pressure. Hydrocarbons contained in subterranean formations are usually at a high pressure. Standard overbalanced drilling techniques require that the hydrostatic pressure in the wellbore exceed the formation pressure, thereby preventing formation or reservoir fluids from flowing uncontrolled into the wellbore.

When the hydrostatic pressure of the drilling fluid is greater than pressure of surrounding formation, a portion of the drilling fluid known commonly as the mud filtrate will tend to penetrate the surrounding formation. The fluid in the formation close to the wellbore will be a mixture of this mud filtrate and the reservoir fluid or formation fluid. The presence of the mud filtrate in the reservoir fluid can interfere with attempts to sample and analyze the reservoir fluid. As a reservoir fluid sample is drawn from the formation at the wall of the wellbore, the first samples of reservoir fluid pumped may comprise primarily mud filtrate, with the amount of mud filtrate in the mixture typically decreasing as pumped volume increases. To avoid collecting mud filtrate in the collected sample, pumping is continued for a period of time before the collection of the fluid sample. Obtaining representative reservoir fluid samples with minimum rig time to determine accurate reservoir fluid properties and contamination while sampling with a formation tester may result in a reduction of overall costs and conservation of resources.

BRIEF DESCRIPTION OF THE DRAWINGS

A more complete understanding of one or more aspects of the present invention and advantages thereof may be acquired by referring to the following description taken in conjunction with the accompanying drawings, in which like reference number indicate like features.

DETAILED DESCRIPTION

Certain aspects and features of the present disclosure relate to contamination estimation of reservoir samples collected via a formation tester. Some methods of contamination estimation may inherently have numerous uncertainties. For example, the density of the formation fluid filtrate is not known. This may lead to inaccurate contamination estimation as errors may exceed 100% in contamination estimation. Also, the fitting of the trend curve may be user dependent which results in a variety of contamination estimates. By accurately estimating contamination, costs of a given operation may be reduced and resources at a well or job site may be conserved.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. The information handling system may also include one or more interface units capable of transmitting one or more signals to a controller, actuator, or like device.

For the purposes of this disclosure, a non-transitory computer-readable media may include any instrumentality or aggregation of instrumentalities that may retain data and/or instructions for a period of time. Computer-readable media may include, for example, without limitation, storage media such as a direct access storage device (for example, a hard disk drive or floppy disk drive), a sequential access storage device (for example, a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 1:
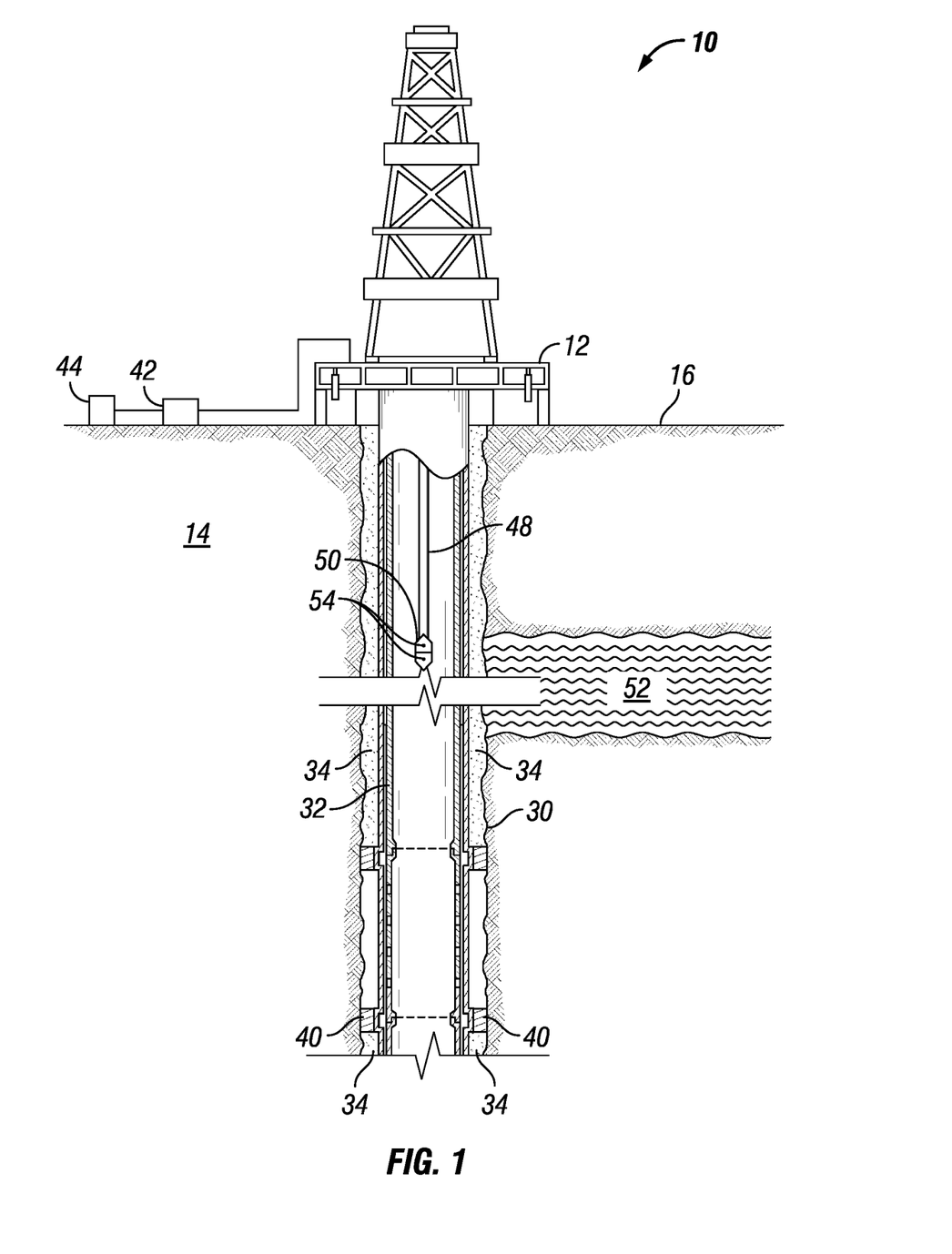
FIG. 1 is a schematic diagram of an apparatus for transferring or retrieving material in a wellbore, according to one or more aspects of the present disclosure.

FIG. 1 is a schematic diagram of an apparatus 10 for transferring or retrieving material in a wellbore 30. Generally, apparatus 10 illustrates a system for transferring material from a surface-located hydrocarbon well site 12 and retrieving material from a surface-located hydrocarbon well site 12. The well site 12 is located over a hydrocarbon bearing formation 14 comprising a hydrocarbon reservoir 52, which is located below a ground surface 16. While well site 12 is illustrated at a ground surface 16, the present disclosure contemplates any one or more embodiments implemented at a well site at any location, including, at sea above a subsea hydrocarbon bearing formation.

The wellbore 30 is formed through various earth strata including the formation 14. A pipe or casing 32 is insertable into the wellbore 30 and may be cemented within the wellbore 30 by cement 34. A pumping system 42 according to one or more aspects of the present disclosure is located at the well site 12. The pumping system 42 may be configured to transfer material, such as reservoir, formation or production fluid, out of the wellbore 30 from, for example, reservoir 52. In one or more embodiments, a formation tester tool 50 is lowered into the wellbore 30 via a conveyance device 48. In one or more embodiments formation tester tool 50 or any other downhole tool (not shown) may comprise one or more sensors 54. The one or more sensors 54 measure one or more properties of downhole fluid (such as formation fluid or drilling fluid) including, but not limited to, density, gas/oil ratio (GOR), condensate/gas ratio (CGR), capacitance, temperature, pressure, one or more gases (for example, methane (C1), ethane (C2), propane (C3), butane (C4), pentane (C5)), one or more hydrocarbon molecules (for example, C6+), resistivity, dielectric, viscosity, and optical sensor data. Any one or more sensors 54 may be sensitive to different types of downhole fluids such as resistivity and dielectric for water-based mud ("WBM") contamination, and density and T1 log mean for oil-based mud ("OBM") contamination. A formation tester tool 50 or any other downhole tool (not shown) may comprise any one or more sensors 54 sensitive to any one or more different types of downhole fluids.

Conveyance device 48 may comprise a wireline, slickline, coiled tubing, jointed tubing or any other conveyance device or combination thereof. Formation tester tool 50 may collect one or more formation fluid samples from wellbore 30. In one or more embodiments, any one or more formation fluid samples collected may be analyzed by control system 44 utilizing any one or more embodiments or aspects of the present disclosure. In one or more embodiments, control system 44 may be located at the well site 12 (as illustrated) or remote from the well site 12. In one or more embodiments, control system 44 may comprise one or more information handling systems comprising one or more programs or instructions, such as the information handling system 200 described with respect to FIG. 2. In one or more embodiments, control system 44 controls the operation of formation tester tool 50 and may process data received from the formation tester tool 50.

Figure 2:
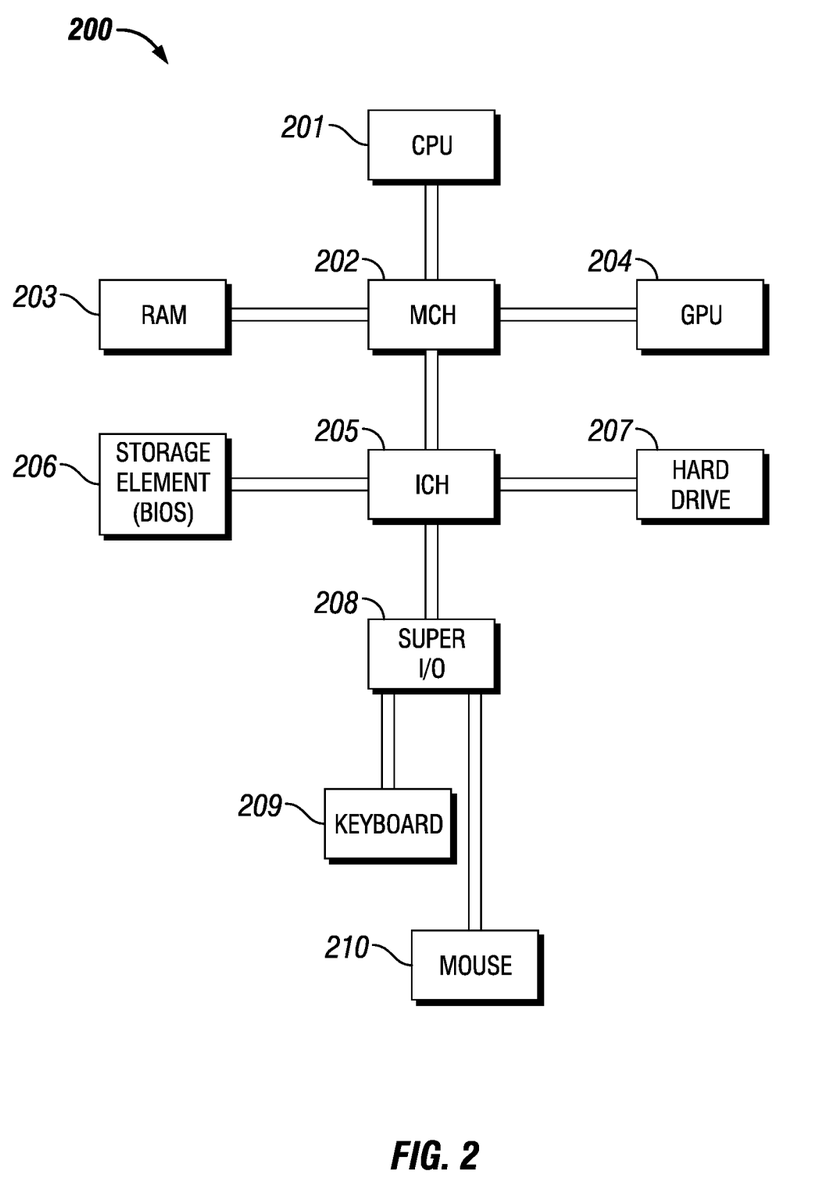
FIG. 2 is a diagram illustrating an example information handling system, according to one or more aspects of the present disclosure.

FIG. 2 is a diagram illustrating an example information handling system 200, according to one or more aspects of the present disclosure. The control system 44 may take a form similar to the information handling system 200 or include one or more components of information handling system 200. A processor or central processing unit (CPU) 201 of the information handling system 200 is communicatively coupled to a memory controller hub (MCH) or north bridge 202. The processor 201 may include, for example a microprocessor, microcontroller, digital signal processor (DSP), application specific integrated circuit (ASIC), or any other digital or analog circuitry configured to interpret and/or execute program instructions and/or process data. Processor 201 may be configured to interpret and/or execute program instructions or other data retrieved and stored in any memory such as memory 203 or hard drive 207. Program instructions or other data may constitute portions of a software or application for carrying out one or more methods described herein. Memory 203 may include read-only memory (ROM), random access memory (RANI), solid state memory, or disk-based memory. Each memory module may include any system, device or apparatus configured to retain program instructions and/or data for a period of time (for example, computer-readable non-transitory media). For example, instructions from a software or application may be retrieved and stored in memory 203, for example, a non-transitory memory, for execution by processor 201.

Modifications, additions, or omissions may be made to FIG. 2 without departing from the scope of the present disclosure. For example, FIG. 2 shows a particular configuration of components of information handling system 200. However, any suitable configurations of components may be used. For example, components of information handling system 200 may be implemented either as physical or logical components. Furthermore, in some embodiments, functionality associated with components of information handling system 200 may be implemented in special purpose circuits or components. In other embodiments, functionality associated with components of information handling system 200 may be implemented in configurable general purpose circuit or components. For example, components of information handling system 200 may be implemented by configured computer program instructions.

Memory controller hub 202 may include a memory controller for directing information to or from various system memory components within the information handling system 200, such as memory 203, storage element 206, and hard drive 207. The memory controller hub 202 may be coupled to memory 203 and a graphics processing unit (GPU) 204. Memory controller hub 202 may also be coupled to an I/O controller hub (ICH) or south bridge 205. I/O controller hub 205 is coupled to storage elements of the information handling system 200, including a storage element 206, which may comprise a flash ROM that includes a basic input/output system (BIOS) of the computer system. I/O controller hub 205 is also coupled to the hard drive 207 of the information handling system 200. I/O controller hub 205 may also be coupled to a Super I/O chip 208, which is itself coupled to several of the I/O ports of the computer system, including keyboard 209 and mouse 210.

In certain embodiments, the control system 44 may comprise an information handling system 200 with at least a processor and a memory device coupled to the processor that contains a set of instructions that when executed cause the processor to perform certain actions. In any embodiment, the information handling system may include a non-transitory computer readable medium that stores one or more instructions where the one or more instructions when executed cause the processor to perform certain actions. As used herein, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a computer terminal, a network storage device, or any other suitable device and may vary in size, shape, performance, functionality, and price. The information handling system may include random access memory (RAM), one or more processing resources such as a central processing unit (CPU) or hardware or software control logic, read only memory (ROM), and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Figure 3:
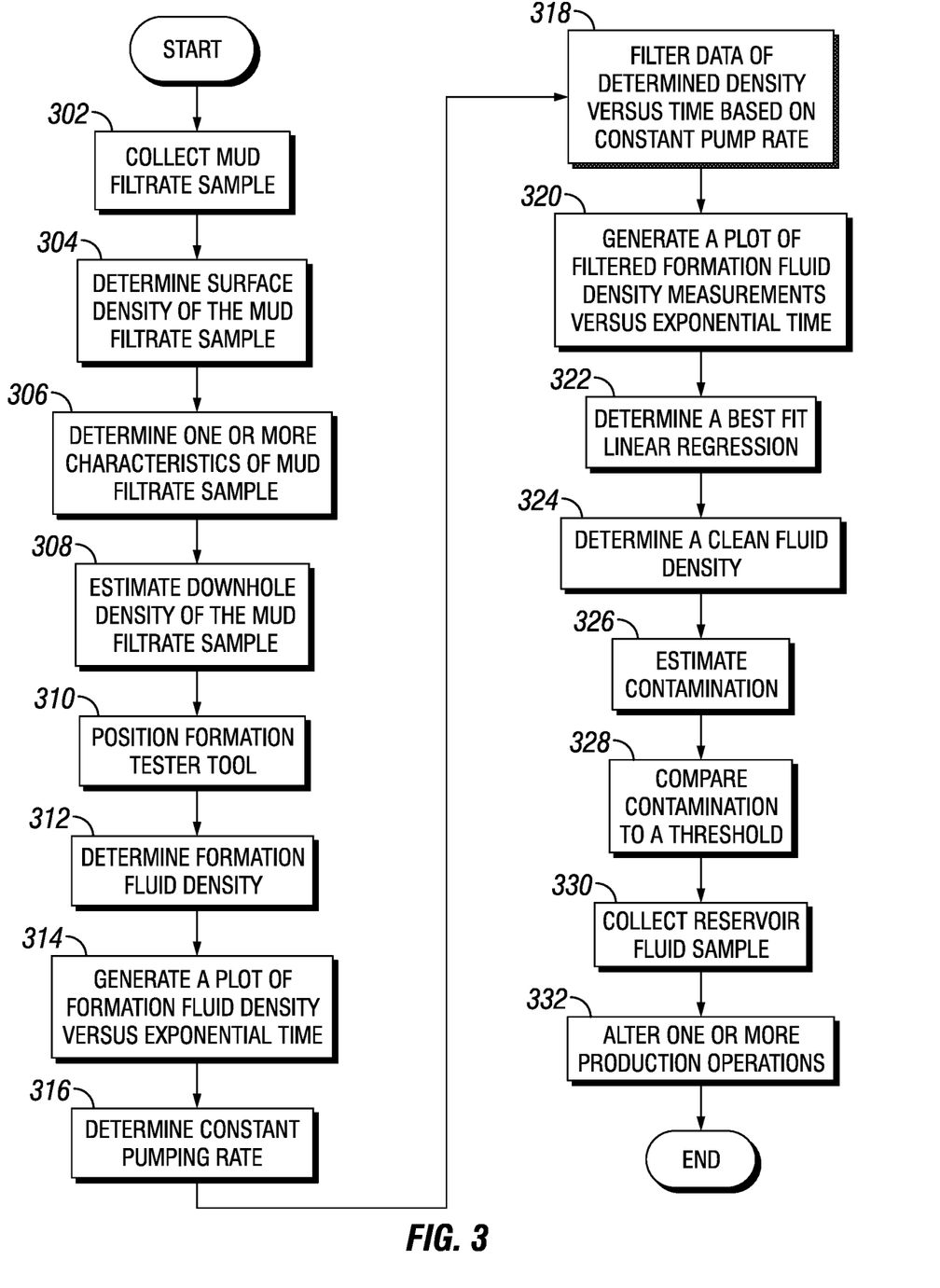
FIG. 3 is a flowchart of a method of contamination estimation, according to one or more aspects of the present disclosure.

FIG. 3 is a flowchart of a method of contamination estimation, according to one or more aspects of the present disclosure. With respect to the description of FIG. 3, references are made to one or more elements of FIGS. 1 and 2. During a drilling operation a portion of the drilling fluid filtrate may penetrate into the formation or the reservoir 52. To properly evaluate a reservoir a representative sample of reservoir fluid is required. High overburden pressure may result in an invasion of drilling fluid into the reservoir which displaces the reservoir fluid. Collection of a representative reservoir fluid may require an estimation of a contamination of the reservoir (for example, contamination of the pumped reservoir fluid) before sampling. For example, formation fluid may comprise drilling fluid, reservoir fluid and any other downhole material or fluid. The formation fluid may be pumped out until a sample of reservoir fluid may be collected. The sample of reservoir fluid may be collected when a contamination of the formation fluid is at or below a threshold level.

In one or more embodiments, at step 302, a mud filtrate sample is collected. The mud filtrate sample may be collected at any time during a well services or production operation at the well site 12. In one or more embodiments, the mud filtrate sample is collected from a mixer, blender, container, tank or any other storage unit or dispenser of the drilling fluid at the surface 16. For example, a filter press may be used to extract the mud filtrate sample from a collected drilling fluid sample. In one or more embodiments, the drilling fluid sample may be collected from a subsurface location and once retrieved to the surface 16 the mud filtrate sample may be extracted. In one or more embodiments, an information handling system may actuate collection of the mud filtrate sample, for example, by transmitting a signal to a device to cause the device to collect the mud filtrate sample.

At step 304, the surface density of the mud filtrate sample is determined. At step 306, one or more characteristics of the mud filtrate sample are determined. A mud filtrate characteristic may comprise any one or more of type of material (for example, any one or more of methane or any other gas, bentonite, oil, one or more synthetic fluids, water, potassium formate or any other material or combination thereof), temperature, density, viscosity, thickness, toughness, slickness or lubricity, permeability, or any other property. In one or more embodiments, the mud filtrate sample is processed by a gas chromatograph to determine a chemical composition of the mud filtrate sample.

At step 308, the downhole density of the mud filtrate sample is estimated based, at least in part, on the one or more characteristics of the mud filtrate sample determined at step 306 and the surface density of the mud filtrate sample determined at step 304. In one or more embodiments, equation of state modeling may be used to identify at a certain pressure and temperature how the mud filtrate will behave downhole, for example, the estimated density of the mud filtrate downhole. In one or more embodiments, correlation of the one or more characteristics may be used to estimate a downhole mud filtrate density for a given temperature and pressure downhole.

At step 310, a downhole tool, such as a formation tester tool 50, is positioned or disposed in wellbore 30. At step 312, density of the formation fluid is determined. For example, density of the formation fluid may be determined as the formation fluid is pumped from the wellbore 30. In one or more embodiments, the formation fluid density may be determined continuously, at any predetermined time interval, in real-time, or at any other time interval as the formation fluid is pumped from the wellbore 30. The formation fluid may comprise reservoir fluid (such as hydrocarbons), mud filtrate, water, any other type of formation fluid or material, or any combination thereof. The density of the formation fluid may be determined based on one or more density measurements from one or more sensors 54. In one or more embodiments, a control system 44 retrieves the one or more density measurements from the one or more sensors 54, the formation tester tool 50, any other downhole tool, or any combination thereof and determines the density of the formation fluid for a given instance of time.

Figure 4:
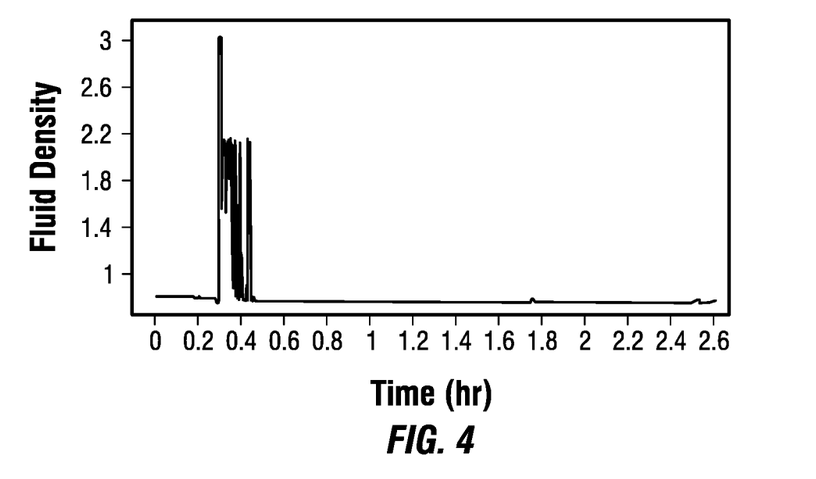
FIG. 4 is a plot illustrating density of formation fluid versus time, according to one or more aspects of the present disclosure.

At step 314, an analysis may be performed or a plot may be generated of the formation fluid density measurements versus exponential time. For example, as illustrated in FIG. 4, density of the formation fluid is plotted for intervals of time according to one or more aspects of the present disclosure. The y-axis or vertical axis (labeled "Fluid Density") indicates the determined density of the formation fluid in grams per cubic centimeter (g/cc) and the x-axis or horizontal axis (labeled "time (hr)") indicates time associated with the determined density in hours ranging from 0 to 2.6 hours.

Figure 5:
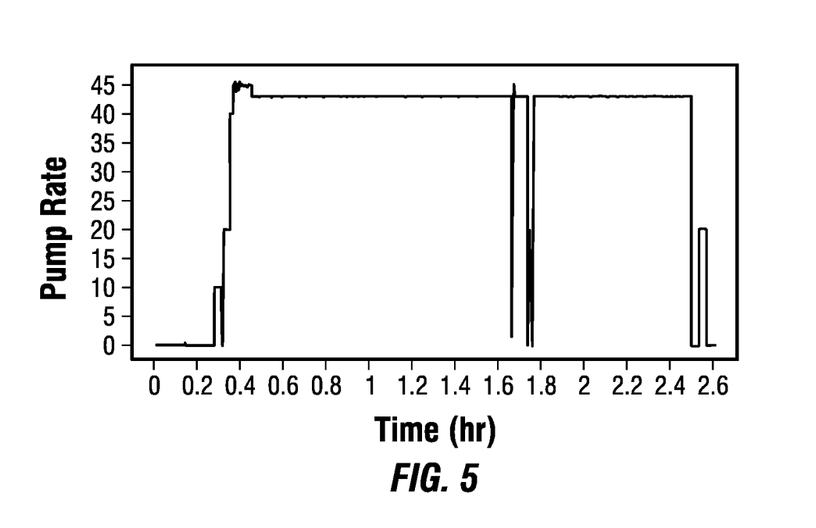
FIG. 5 is a plot illustrating pump rate versus time, according to one or more aspects of the present disclosure.

At step 316, a constant pump rate is determined. A correlation may be made between the determined pump rate at each interval of time to determine the constant pumping rate for a given operation, snapshot of time or predetermined timed interval. The pumping rate may be determined using any one or more formulas or methods known in the field of art or as provided in material or instructions associated with a given pump. FIG. 5 illustrates a plot of determined pumping rates versus time according to one or more aspects of the present disclosure. The y-axis or vertical axis (labeled "Pump Rate") indicates the rate of pumping of the formation fluid from the wellbore 30 cubic centimeters per second (cc/s) and the x-axis or horizontal axis (labeled "time(hr)") indicates time in hours associated with the determined pump rate ranging from 0 to 2.6 hours.

Figure 6:
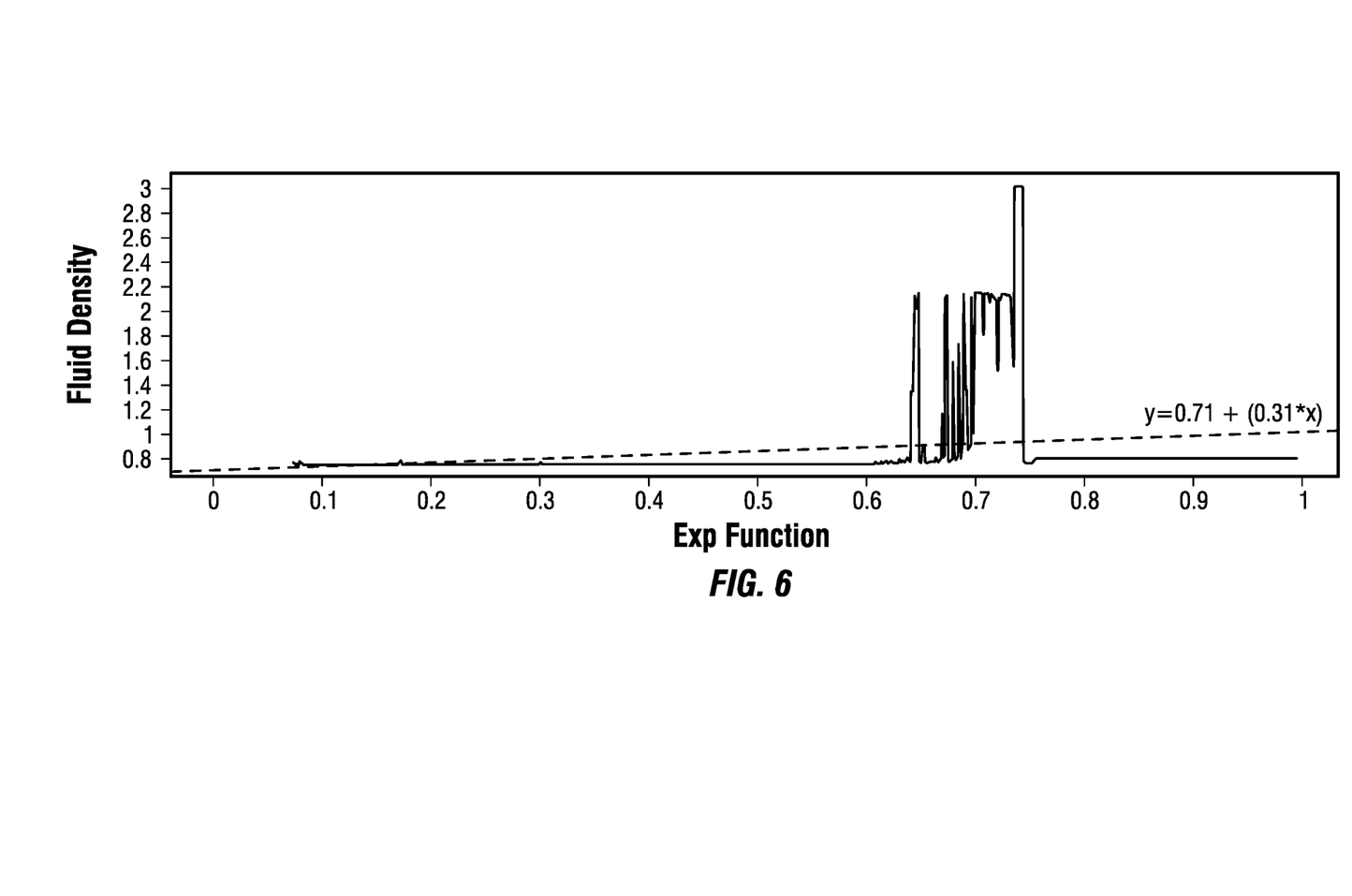
FIG. 6 is a plot illustrating density of the formation fluid versus exponential function of time, according to one or more aspects of the present disclosure.

FIG. 6 illustrates the density of the formation fluid versus exponential function of time. The y-axis or vertical axis (labeled "Fluid Density") indicates the density of formation fluid and the x-axis or horizontal axis (labeled "Exp Function") indicates an exponential function of time. The constant pumping rate may be determined by determining a pumping rate at which a plurality of pumping rates associated with a predetermined time interval are within a range of deviation of each other. For example, as illustrated in FIG. 5, if the range of deviation is five for an interval of time of 2.5 hours then the pumping rate is a range between 1 and 45 during time at or about 0.4 hours to at or about 2.5 hours. The constant pumping rate may then be determined by using any analysis or modeling including, but not limited to, mean, median, average or any other mathematical model, or combination thereof. For example, the constant pumping rate may be determined to be 42.5 when the pumping rate is within a range of 40 to 45.

Figure 7:
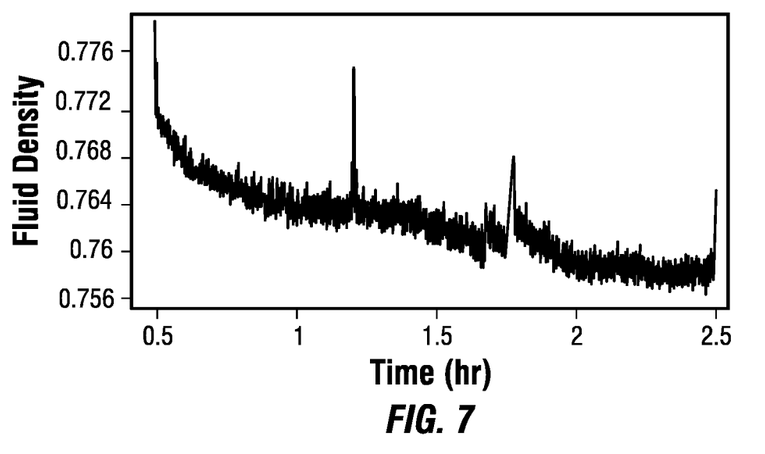
FIG. 7 is a plot illustrating density of formation fluid versus time at a constant pump rate, according to one or more aspects of the present disclosure.
Figure 8:
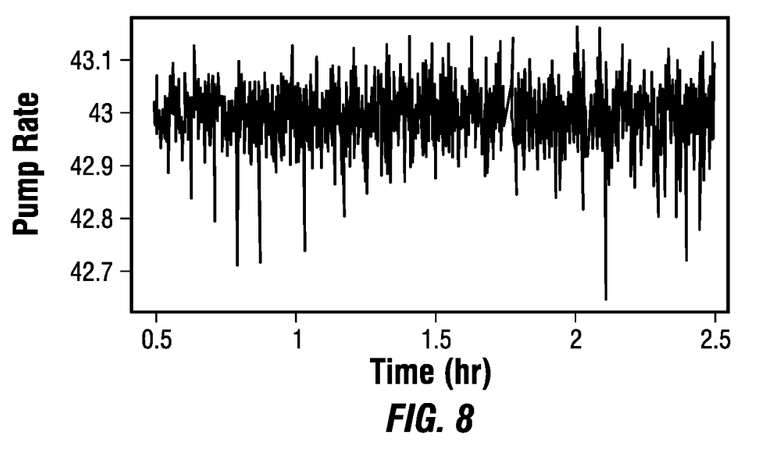
FIG. 8 is a plot illustrating constant pump rate versus time, according to one or more aspects of the present disclosure.

At step 318, the data associated with the determined density of the formation fluid versus time (for example, data illustrated in FIG. 4) is filtered based on the determined constant pumping rate. FIG. 7 is a plot illustrating density of formation fluid versus time at a constant pump rate, according to one or more aspects of the present disclosure. FIG. 7 illustrates a range of determined density versus time from FIG. 4 at a finer scale on the y-axis so that deviations in the determined densities associated with the range of time correlating to the determined constant pump rate are highlighted. FIG. 7 illustrates a trend over time as opposed to a determination of exact fluid density values. FIG. 8 is a plot illustrating constant pumping rate versus time, according to one or more aspects of the present disclosure. FIG. 8 illustrates a range of pumping rates versus time from FIG. 5 at a finer scale on the y-axis so that deviations in the determined pumping rates associated with the range of time correlating to the determined constant pump rate are highlighted. FIG. 8 illustrates a trend over time as opposed to a determination of exact pump rate.

Figure 9:
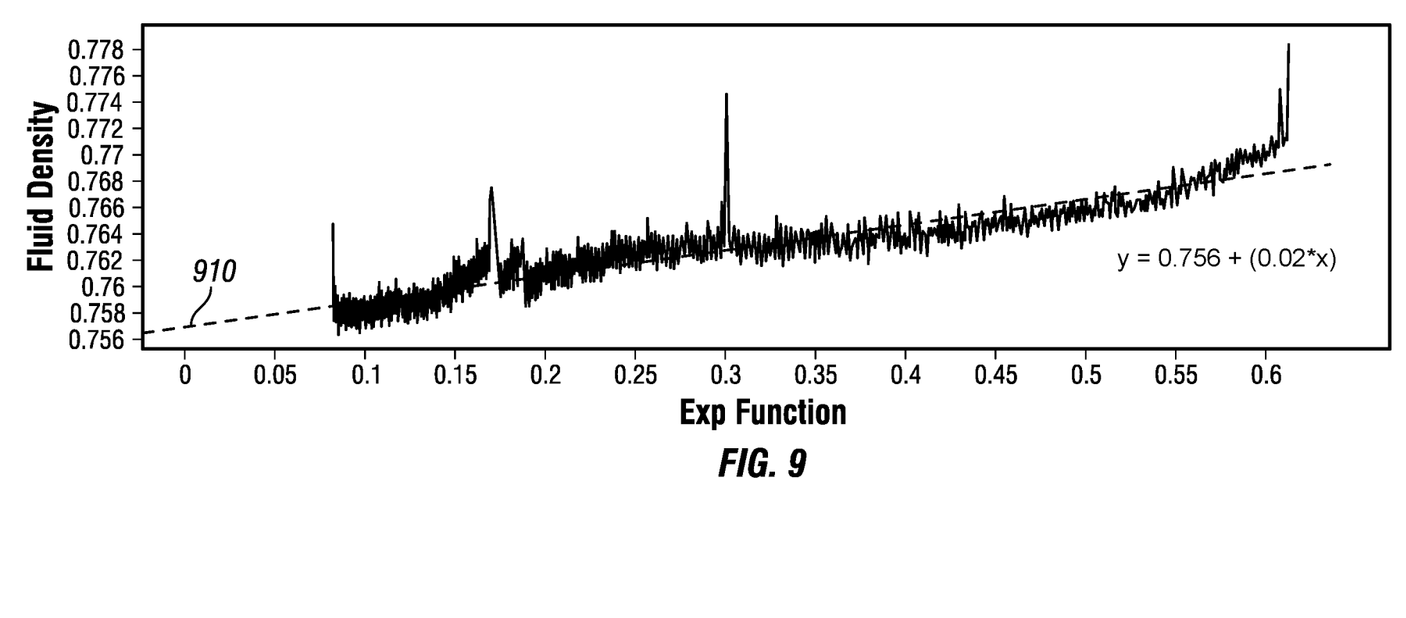
FIG. 9 is a plot illustrating density of the formation fluid versus exponential function of time filtered at a constant rate, according to one or more aspects of the present disclosure.

At step 320, a plot is generated or an analysis is performed of the determined plurality of fluid densities associated with the determined constant pumping rate versus an exponential function of time corresponding to the constant pumping rate. Using the plot or analysis from step 320, at step 322 a best fit linear regression is determined. For example, FIG. 9 illustrates a plot of determined fluid density versus the exponential function of time corresponding to the constant pumping rate. A best fit linear regression line is indicated at 910. At step 324, a clean fluid density is determined based, at least in part, on the determined density of the formation fluid at the constant pumping rate for an interval of time. For example, a linear regression is extrapolated for the determined density of the formation fluid versus exponential time corresponding to the constant pumping rate. At step 324, the linear regression is extrapolated, for example, for a time "t" where "t" approaches infinity. In FIG. 9, the clean fluid density where the exponential function of time approaches or is zero correlates to a density of at or about 0.756.

At step 326, the contamination of the formation fluid is estimated based, at least in part, on the clean fluid density. In one or more embodiments, the contamination may be estimated using a material balance equation or ratio, such as, $C=(\rho_{rt}-\rho_{cf})/(\rho_{mf}-\rho_{cf})$, where C is the estimated contamination, it is the value of a current density measurement, for example, a real-time formation fluid density measurement, $\rho_{rt}$ is the clean fluid density and $\rho_{mf}$ is the estimated downhole mud filtrate density, for example, the estimated downhole mud filtrate density from step 308. In one or more embodiments, an estimated pump-out time may be determined based, at least in part, on the estimated contamination and a trend of the estimated contamination.

At step 328, the estimated contamination or a value based, at least in part, on the estimated contamination is compared to a predetermined contamination threshold. At step 330, a reservoir fluid sample is collected based on the comparison at step 328. For example, a contamination threshold may be indicative of or correspond to 0.20 (20%), 0.05 (5%) or any other value above or below. When the estimated contamination is at or below the threshold, a reservoir fluid sample may be collected.

At step 332, one or more production operations or a well servicing operation may be altered based, at least in part, on the collected reservoir fluid sample. In one or more embodiments, the collected reservoir sample may be compared to another reservoir fluid sample from a nearby well to determine likelihood that the two wells are connected. In one or more embodiments, one or more of the facilities design (for example, one or more of separate design, flow line design, injection program for well for asphalt treatment, general design of the wellbore surface facilities, or any other parameter of facilities design), flow assurance or reserve estimation may be altered based, at least in part, on the collected reservoir fluid sample. In one or more embodiments, another well may be drilled based, at least in part, on the collected reservoir fluid sample. In one or more embodiments, the reservoir fluid sample may be sent to a laboratory for further testing or evaluation. In one or more embodiments, any one or more steps of FIG. 3 may not be implemented or may be implemented in any order.

While downhole density is discussed, the present disclosure contemplates that in one or more embodiments any one or more measurements from any one or more sensors positioned on or deployed within formation tester tool 50 may be utilized to determine the contamination estimation in lieu of the downhole density.

In one or more embodiments, a method for contamination estimation comprises collecting a mud filtrate sample, determining a surface density of the mud filtrate sample, estimating downhole density of the mud filtrate sample based, at least in part, on the surface density, determining a plurality of formation fluid densities for a period of time, determining the constant pumping rate, filtering the determined formation fluid density based, at least in part, on the constant pumping rate, determining a clean fluid density based, at least in part, on a linear regression of the filtered determined formation fluid density versus an exponential function of time, estimating a contamination based, at least in part, on the clean fluid density, comparing the estimated contamination to a contamination threshold and collecting a reservoir fluid sample based, at least in part, on the comparison. In one or more embodiments, the method of contamination estimation comprises receiving one or more formation fluid density measurements from one or more sensors, wherein the determined formation fluid density is based on the one or more formation fluid density measurements. In one or more embodiments, the method of contamination estimation further comprises positioning a formation tester tool within a wellbore, wherein the formation tester tool collects the reservoir fluid sample. In one or more embodiments, the method of contamination estimation further comprises determining one or more mud filtrate characteristics of the mud filtrate sample, wherein the estimated downhole density of the mud filtrate sample is based, at least in part, on at least one of the one or more mud filtrate characteristics. In one or more embodiments, wherein determining the constant pumping rate comprises determining a pumping rate at which a plurality of pumping rates associated with a predetermined interval of time are within a range of deviation. In one or more embodiments, the clean fluid density is determined based, at least in part, on extrapolation of the linear regression for a time that approaches infinity. In one or more embodiments, estimating the contamination comprises calculating a first calculated density, calculating a second calculated density and dividing the first calculated density by the second calculated density, wherein calculating the first calculated density comprises subtracting from a real-time formation fluid density measurement the clean fluid density, and wherein calculating the second calculated density comprises subtracting from the estimated mud filtrated density the clean fluid density. In one or more embodiments, the intensifier comprises a plurality of intensifiers, and wherein distribution of the hydraulic fluid to each of the plurality of intensifiers is based, at least in part, on a fuel map.

In one or more embodiments, non-transitory computer-readable medium storing one or more executable instructions that, when executed, cause one or more processors to actuate collection of a mud filtrate sample, determine a surface density of the mud filtrate sample, estimate downhole density of the mud filtrate sample based, at least in part, on the surface density, determine a plurality of formation fluid densities for a period of time, determining a constant pumping rate, filter the determined formation fluid density based, at least in part, on the constant pumping rate, determine a clean fluid density based, at least in part, on a linear regression of the filtered determined formation fluid density versus an exponential function of time, estimate a contamination based, at least in part, on the clean fluid density, compare the estimated contamination to a contamination threshold, and collect a reservoir fluid sample based, at least in part, on the comparison. In one or more embodiments, the one or more executable instructions that, when executed, further cause the one or more processors to receive one or more formation fluid density measurements from one or more sensors, wherein the determined formation fluid density is based on the one or more formation fluid density measurements. In one or more embodiments, the one or more executable instructions that, when executed, further cause the one or more processors to position a formation tester tool within a wellbore, wherein the formation tester tool collects the reservoir fluid sample. In one or more embodiments, the one or more executable instructions that, when executed, further cause the one or more processors to determine one or more mud filtrate characteristics of the mud filtrate sample, wherein the estimated downhole density of the mud filtrate sample is based, at least in part, on at least one of the one or mud filtrate characteristics. In one or more embodiments, determining a constant pumping rate comprises determining a pumping rate at which a plurality of pumping rates associated with a predetermined interval of time are within a range of deviation. In one or more embodiments, the clean fluid density is determined based, at least in part, on extrapolation of the linear regression for a time that approaches infinity. In one or more embodiments, estimating the contamination comprises calculating a first calculated density, calculating a second calculated density and dividing the first calculated density by the second calculated density, wherein calculating the first calculated density comprises subtracting from a real-time formation fluid density measurement the clean fluid density, and wherein calculating the second calculated density comprises subtracting from the estimated mud filtrated density the clean fluid density. In one or more embodiments, the intensifier comprises a plurality of intensifiers, and wherein distribution of the hydraulic fluid to each of the plurality of intensifiers is based, at least in part, on a fuel map. In one or more embodiments, the intensifier comprises a plurality of intensifiers, and wherein distribution of the hydraulic fluid to each of the plurality of intensifiers is based, at least in part, on a fuel map.

In one or more embodiments, a system for contamination estimation comprises a mud filtrate sample, a processor, a non-transitory memory coupled to the processor, the non-transitory memory comprising one or more instructions that, when executed by the processor, cause the processor to determine a surface density of the mud filtrate sample, estimate downhole density of the mud filtrate sample based, at least in part, on the surface density, determine a plurality of formation fluid densities for a period of time, determine a constant pumping rate, filter the determined formation fluid density based, at least in part, on the constant pumping rate, determine a clean fluid density based, at least in part, on a linear regression of the filtered determined formation fluid density versus an exponential function of time, estimate a contamination based, at least in part, on the clean fluid density, compare the estimated contamination to a contamination threshold and collect a reservoir fluid sample based, at least in part, on the comparison. In one or more embodiments, the one or more instructions that, when executed by the processor, further cause the processor to receive one or more formation fluid density measurement from one or more sensors, wherein the determined formation fluid density is based on the one or more formation fluid density measurements. In one or more embodiments, the one or more instructions that, when executed by the processor, further cause the processor to determine one or more mud filtrate characteristics of the mud filtrate sample, wherein the estimated downhole density of the mud filtrate sample is based, at least in part, on at least one of the one or mud filtrate characteristics. In one or more embodiments, estimating the contamination comprises calculating a first calculated density, calculating a second calculated density and dividing the first calculated density by the second calculated density, wherein calculating the first calculated density comprises subtracting from a real-time formation fluid density measurement the clean fluid density, and wherein calculating the second calculated density comprises subtracting from the estimated mud filtrated density the clean fluid density.

The foregoing description of certain aspects, including illustrated aspects, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method for contamination estimation, comprising:
collecting or extracting a mud filtrate sample at a subsurface location;
retrieving the mud filtrate sample at a surface;
determining a surface density of the mud filtrate sample at the surface;
estimating downhole density of the mud filtrate sample based, at least in part, on the surface density for a given temperature and a pressure downhole;
determining a plurality of formation fluid densities for a period of time;
determining a constant pumping rate, wherein the constant pumping rate is based on a pumping rate at which a plurality of pumping rates associated with a predetermined time interval are within a range of deviation of each other;
filtering the determined plurality of formation fluid densities based, at least in part, on the constant pumping rate;
performing an analysis of the determined plurality of fluid densities at the constant pumping rate versus an exponential function of time to determine a best fit linear regression, wherein all of the analysis is performed at the constant pump rate, wherein the constant pump rate is predetermined from a median or an average of the plurality of pump rates;
determining a clean fluid density based, at least in part, on the best fit linear regression;
estimating a contamination based, at least in part, on dividing a first calculated density by a second calculated density, wherein the first calculated density comprises subtracting from the clean fluid density from a real-time formation fluid density measurement, and wherein the second calculated density comprises subtracting the clean fluid density from the estimated mud filtrate density;
estimating a pump-out time based, at least in part, on the estimated contamination and a trend of the estimated contamination;
comparing the estimated contamination to a contamination threshold, wherein the contamination threshold is about 20%; and
collecting a reservoir fluid sample based, at least in part, on the comparison, wherein the reservoir fluid sample is collected when the estimated contamination is at or below the contamination threshold.

2. The method of contamination estimation of claim 1, further comprising receiving one or more formation fluid density measurements from one or more sensors, wherein the determined plurality of formation fluid densities is based on the one or more formation fluid density measurements.

3. The method of contamination estimation of claim 1, further comprising positioning a formation tester tool within a wellbore, wherein the formation tester tool collects the reservoir fluid sample.

4. The method of contamination estimation of claim 1, further comprising determining one or more mud filtrate characteristics of the mud filtrate sample, wherein the estimated downhole density of the mud filtrate sample is based, at least in part, on at least one of the one or more mud filtrate characteristics.

5. The method of contamination estimation of claim 4, wherein the one or more mud filtrate characteristics comprise at least one of type of material, chemical composition, temperature, density, viscosity, thickness, toughness, slickness, and permeability.

6. The method of contamination estimation of claim 1, wherein determining the constant pumping rate comprises determining a pumping rate at which a plurality of pumping rates associated with a predetermined interval of time are within a range of deviation.

7. The method of contamination estimation of claim 1, wherein the clean fluid density is determined based, at least in part, on extrapolation of the linear regression for a time that approaches infinity.

8. A non-transitory computer-readable medium storing one or more executable instructions that, when executed, cause one or more processors to:
actuate collection or extraction of a mud filtrate sample at a subsurface location;
instruct a formation tester tool to retrieve the mud filtrate sample at a surface;
determine a surface density of the mud filtrate sample at the surface;
estimate downhole density of the mud filtrate sample based, at least in part, on the surface density for a given temperature and a pressure downhole;
determine a plurality of formation fluid densities for a period of time;
determine a constant pumping rate, wherein the constant pumping rate is based on a pumping rate at which a plurality of pumping rates associated with a predetermined time interval are within a range of deviation of each other;
filter the determined plurality of formation fluid densities based, at least in part, on the constant pumping rate;
perform an analysis of the determined plurality of fluid densities associated at the constant pumping rate versus an exponential function of time to determine a best fit linear regression, wherein all of the analysis is performed at the constant pump rate, wherein the constant pump rate is predetermined from a median or an average of the plurality of pump rates;
determine a clean fluid density based, at least in part, on a linear regression of the filtered determined plurality of formation fluid densities versus an exponential function of time corresponding to the constant pumping rate;
estimate a contamination based, at least in part, on dividing a first calculated density by a second calculated density, wherein the first calculated density comprises subtracting the clean fluid density from a real-time formation fluid density measurement, and wherein the second calculated density comprises subtracting the clean fluid density from the estimated mud filtrate density;
estimate a pump-out time based, at least in part, on the estimated contamination and a trend of the estimated contamination;
compare the estimated contamination to a contamination threshold, wherein the contamination threshold is about 20%; and
collect a reservoir fluid sample based, at least in part, on the comparison, wherein the reservoir fluid sample is collected when the estimated contamination is at or below the contamination threshold.

9. The non-transitory computer-readable medium of claim 8, wherein the one or more executable instructions that, when executed, further cause the one or more processors to receive one or more formation fluid density measurements from one or more sensors, wherein the determined plurality of formation fluid densities is based on the one or more formation fluid density measurements.

10. The non-transitory computer-readable medium of claim 8, wherein the one or more executable instructions that, when executed, further cause the one or more processors to position a formation tester tool within a wellbore, wherein the formation tester tool collects the reservoir fluid sample.

11. The non-transitory computer-readable medium of claim 8, wherein the one or more executable instructions that, when executed, further cause the one or more processors to determine one or more mud filtrate characteristics of the mud filtrate sample, wherein the estimated downhole density of the mud filtrate sample is based, at least in part, on at least one of the one or mud filtrate characteristics.

12. The non-transitory computer-readable medium of claim 11, wherein the one or more mud filtrate characteristics comprise at least one of type of material, temperature, density, viscosity, thickness, toughness, slickness, and permeability, and wherein the one or more mud filtrate characteristics comprise at least one of a type of material, a chemical composition, a temperature, a density, a viscosity, a thickness, a toughness, a lubricity and a permeability.

13. The non-transitory computer-readable medium of claim 8, wherein determining the constant pumping rate comprises determining a pumping rate at which a plurality of pumping rates associated with a predetermined interval of time are within a range of deviation.

14. The non-transitory computer-readable medium of claim 8, wherein the clean fluid density is determined based, at least in part, on extrapolation of the linear regression for a time that approaches infinity.

15. A system for contamination estimation, comprising:
a mud filtrate sample, wherein the mud filtrate sample is collected or extracted at a subsurface location;
a formation tester tool configured to retrieve the mud filtrate sample at a surface;
a processor;
a non-transitory memory coupled to the processor, the non-transitory memory comprising one or more instructions that, when executed by the processor, cause the processor to:
determine a surface density of the mud filtrate sample at the surface;
estimate downhole density of the mud filtrate sample based, at least in part, on the surface density for a given temperature and a pressure downhole;
determine a plurality of formation fluid densities for a period of time;
determine a constant pumping rate, wherein the constant pumping rate is based on a pumping rate at which a plurality of pumping rates associated with a predetermined time interval are within a range of deviation of each other;
filter the determined plurality of formation fluid densities based, at least in part, on the constant pumping rate;
perform an analysis of the determined plurality of fluid densities associated at the constant pumping rate versus an exponential function of time to determine a best fit linear regression, wherein all of the analysis is performed at the constant pump rate, wherein the constant pump rate is predetermined from a median or an average of the plurality of pump rates;
determine a clean fluid density based, at least in part, on a linear regression of the filtered determined plurality of formation fluid densities versus an exponential function of time corresponding to the constant pumping rate;
estimate a contamination based, at least in part, on dividing a first calculated density by a second calculated density, wherein the first calculated density comprises subtracting the clean fluid density from a real-time formation fluid density measurement, and wherein the second calculated density comprises subtracting the clean fluid density from the estimated mud filtrate density;
estimate a pump-out time based, at least in part, on the estimated contamination and a trend of the estimated contamination;
compare the estimated contamination to a contamination threshold, wherein the contamination threshold is about 20%; and
collect a reservoir fluid sample based, at least in part, on the comparison, wherein the reservoir fluid sample is collected when the estimated contamination is at or below the contamination threshold.

16. The system for contamination estimation of claim 15, wherein the one or more instructions that, when executed by the processor, further cause the processor to receive one or more formation fluid density measurement from one or more sensors, wherein the determined plurality of formation fluid densities is based on the one or more formation fluid density measurements.

17. The system for contamination estimation of claim 15, wherein the one or more instructions that, when executed by the processor, further cause the processor to determine one or more mud filtrate characteristics of the mud filtrate sample, wherein the estimated downhole density of the mud filtrate sample is based, at least in part, on at least one of the one or more mud filtrate characteristics, and wherein the one or more mud filtrate characteristics comprise at least one of a type of material, a chemical composition, a temperature, a density, a viscosity, a thickness, a toughness, a lubricity and a permeability.

* * * * *